(12) United States Patent
New et al.

(10) Patent No.: US 6,368,619 B1
(45) Date of Patent: *Apr. 9, 2002

(54) HYDROPHOBIC PREPARATIONS OF HYDROPHILIC SPECIES AND PROCESS FOR THEIR PREPARATION

(75) Inventors: Roger Randal Charles New, London; Christopher John Kirby, Berkshire, both of (GB)

(73) Assignee: Provalis UK Limited (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/648,065

(22) PCT Filed: Nov. 14, 1994

(86) PCT No.: PCT/GB94/02495

§ 371 Date: May 15, 1996

§ 102(e) Date: May 15, 1996

(87) PCT Pub. No.: WO95/13795

PCT Pub. Date: May 26, 1995

(30) Foreign Application Priority Data

Nov. 16, 1993 (GB) ............................................. 9323588

(51) Int. Cl.$^7$ ........................ A61K 9/127; A61K 9/133; A61K 38/00
(52) U.S. Cl. ..................... 424/450; 424/94.3; 424/812; 514/2; 514/3; 514/6; 514/8; 514/21; 514/44; 514/937; 935/54; 264/4.1; 264/4.3
(58) Field of Search ................................. 424/400, 450, 424/94.3, 812; 264/4.1, 4.3, 4.6; 436/829; 514/2, 3, 6, 8, 21, 937; 935/54

(56) References Cited

U.S. PATENT DOCUMENTS 4,743,449 A * 5/1988 Yoshida ...................... 424/420

| 5,077,069 A | 12/1991 | Chang et al. |
| 5,084,289 A | 1/1992 | Shin et al. |

FOREIGN PATENT DOCUMENTS

| EP | 0 521 562 A1 | 1/1993 |
| EP | 0 326 829 | 4/1994 |
| FR | 2381 520 | 9/1978 |
| FR | 2 519 864 | 7/1983 |
| WO | 86/02264 | 4/1986 |
| WO | WO 92/00019 | 1/1992 |
| WO | WO 96/14871 | 5/1996 |
| WO | WO 96/17593 | 6/1996 |
| WO | WO 96/17594 | 6/1996 |
| WO | WO 96/17899 | 6/1996 |

OTHER PUBLICATIONS

Kirk–Othmer, Encyclopedia of Chemical Technology, Third Ed., "Surfactants and Defensive Systems", 22: 341–348, 1983.

Luisi, Angew. Chem. Int. Ed. Engl., "Enzymes Hosted in Reverse Micelles in Hydrocarbon Solution", 24(6):439–450, 1983.

Ullmann's Encyclopedia of Industrial Chemistry, Fifth ed., "Surfactants", A25:752–758, 1994.

* cited by examiner

Primary Examiner—Gollamudi S. Kishore
(74) Attorney, Agent, or Firm—Pennie & Edmonds LLP

(57) ABSTRACT

Single phase preparations of hydrophilic species, in particular macromolecular compounds such as proteins or glycoproteins in a hydrophobic solvent such as an oil can be obtained by preparing a hydrophile/amphiphile array in which the hydrophilic head groups of the amphiphile are orientated towards the hydrophilic species and bringing the array into contact with the hydrophobic solvent. The preparations of the invention can be used alone or can be combined with an aqueous phase to form emulsions in which the hydrophilic species is present in the hydrophobic phase. The compositions of the present invention are versatile and have application in the pharmaceutical, food, cosmetic, chemical and agricultural industries.

20 Claims, No Drawings

HYDROPHOBIC PREPARATIONS OF HYDROPHILIC SPECIES AND PROCESS FOR THEIR PREPARATION

This application is a 371 of PCT/GB/94/02695 filed Nov. 14, 1994.

The present invention relates to preparations of substances in hydrophobic solvents in which they would not normally be soluble and to processes for obtaining these preparations. In particular, the invention relates to preparations of hydrophilic species in hydrophobic solvents such as oils.

The invention in particular applies to hydrophilic macromolecules which would not normally be soluble in oils or other hydrophobic solvents.

For many applications, e.g in the pharmaceutical sciences, in food technology or the cosmetics industry, work with proteins and similar macromolecules presents problems because their hydrophilicity and high degree of polarity limit the extent to which they can interact with or incorporate into lipid phases. Many natural systems employ lipidic barriers (eg skin, cell membranes) to prevent access of hydrophilic molecules to internal compartments; the ability to disperse proteins in lipidic vehicles would open up a new route to introduction of these macromolecules into biological systems, whereby the lipid medium containing the protein can integrate with the hydrophobic constituents of barriers, instead of being excluded by them.

Another area where dissolution of proteins into oils may confer advantage is for the use of enzymes in organic phases. Enzymic syntheses are becoming increasingly important compared to chemical processes because of their much lower energy needs, greater substrate and product specificities, high yields, and the fact that many reactions are catalysed which are impossible by chemical means. Recent findings that enzymes can remain active in organic environments have opened up many additional possibilities. Thus, reactions involving lipophilic substrates and products may be catalysed effectively, and enzyme stability is often much greater than in aqueous environments, allowing them to be used in much more extreme conditions such as at high temperature. A very important aspect is that reactions involving hydrolytic enzymes such as lipases and peptidases can preferentially go in the reverse direction in low water environments, thus enabling the synthesis of a wide range of industrially important compounds. Another application is where a complex chain of reactions is involved in which the multiple catalytic units need to be maintained in close proximity to each other. Such might be the case in light-initiated redox reactions. An additional possibility is the controlled production of nanoparticulates in oil phase, using enzymes to induce (mineralisation by action on organometallic substrates. The preparation of a stable dispersion of preformed nanoparticulates in oil phase may also be advantageous for the performance of certain surface-catalysed reactions.

Dispersion of hydrophilic substances in oil phase rather than aqueous media confers other benefits in terms of increasing their stability with respect to temperature-mediated denaturation, hydrolysis, light sensitivity etc. Oils can be chosen which remain fluid over a wider temperature range than aqueous solutions, or that have a higher viscosity, resulting in greater protection against physical damage. In mixed-phase systems, sequestration of proteins in oil can limit mutually harmful interactions—eg oxidation—with water-soluble compounds.

There are examples of formulations containing both macromolecules and oil and one such example is disclosed in EP-A-0366277. The formulation disclosed in this document is an emulsion having both a hydrophobic and a hydrophilic phase, wherein the hydrophobic phase contains chylomicra or chylomicron-forming lipids. However, the macromolecule is dissolved in the hydrophilic phase not in the hydrophobic phase.

EP-A-0521994 also relates to a composition suitable for the oral delivery of macromolecules which comprises a biologically active material in association with lecithin or a compound capable of acting as a precursor for lecithin in vivo. All of the compositions exemplified are formulations which comprise a hydrophilic and a lipophilic phase. Once again, in this prior art document, the macromolecule is dissolved in the hydrophilic phase rather than in the lipophilic phase.

Although the formulations mentioned above do contain both macromolecules and oils, it is significant that in all cases the macromolecule is dissolved in the hydrophilic rather than in the lipophilic phase. Attempts to form true solutions of macromolecules in oils have met with limited success.

The present invention relates to the surprising discovery that if a hydrophilic species is mixed with an amphiphile under certain conditions, the resultant composition will be readily soluble in lipophilic solvents as oils.

In a first aspect of the present invention there is provided a process for the preparation of a single phase hydrophobic preparation comprising a hydrophilic species, in a hydrophobic solvent, the process comprising:

(i) associating the hydrophilic species with an amphiphile in a liquid medium such that, in the liquid medium, there is no chemical interaction between the amphiphile and the hydrophilic species;

(ii) removing the liquid medium to leave an array of amphiphile molecules with their hydrophilic head groups orientated towards the hydrophilic species; and (iii) providing a hydrophobic solvent around the hydrophilic species/amphiphile array.

In the context of the present invention, the term "chemical interaction" relates to an interaction such as a covalent or ionic bond or a hydrogen bond. It is not intended to include van der Waals forces or other interactions of that order of magnitude.

It has been found that the order in which the components of the preparation are mixed is particularly important. In one attempt to prepare a molecular dispersion, we mixed a macromolecular compound (an example of a hydrophilic species) with the hydrophobic solvent and then added amphiphile whilst in an alternative procedure, a macromolecular compound was added to a mixture of the hydrophobic solvent and the amphiphile. However, both of these approaches result in the production of a grainy dispersion of the macromolecular compound in the solvent rather than in a true molecular dispersion. It was found that only by adding the macromolecular compound to the amphiphile in such a way that an array is produced in which the hydrophilic head groups of the amphiphile are orientated towards the macromolecule and then dissolving this array in the hydrophobic solvent, could a single phase preparation be produced.

As mentioned above, the hydrophilic species and the amphiphile are associated in a liquid medium and in many cases the array is formed in the liquid medium before it is removed. This occurs when the amphiphile and liquid medium are such that the array is formed in the liquid medium even in the absence of a hydrophilic species.

In the present invention the term "hydrophilic species" relates to any species which is generally soluble in aqueous solvents but insoluble in hydrophobic solvents. The range of hydrophilic species of use in the present invention is diverse but hydrophilic macromolecules represent an example of a species which may be used.

A wide variety of macromolecules is suitable for use in the present invention. In general, the macromolecular compound will b e hydrophilic or will at least have hydrophilic regions since there is usually little difficulty in solubilising a hydrophobic macromolecule in oily solutions. Examples of suitable macromolecules include proteins and glycoproteins, oligo and polynucleic acids, for example DNA and RNA, polysaccharides and supramolecular assemblies of any of these including, in some cases, whole cells or organelles. It may also be convenient to co-solubilise a small molecule such as a vitamin in association with a macromolecule, particularly a polysaccharide such as a cyclodextrin. Small molecules such as vitamin B12 may also be chemically conjugated with macromolecules and may thus be included in the compositions.

Examples of particular proteins which may be successfully solubilised by the method of the present invention include insulin, calcitonin, haemoglobin, cytochrome C, horseradish peroxidase, aprotinin, mushroom tyrosinase, erythropoietin, somatotropin, growth hormone, growth hormone releasing factor, galanin, urokinase, Factor IX, tissue plasminogen activator, superoxide dismutase, catalase, peroxidase, ferritin, interferon, Factor VIII and fragments thereof (all of the above proteins can be from any suitable source). Other macromolecules may be used are FITC-labelled dextran and RNA extract from Torulla yeast.

It seems that there is no upper limit of molecular weight for the macromolecular compound since dextran having a molecular weight of about 1,000,000 can easily be solubilised by the process of the present invention.

In addition to macromolecules, the process of the present invention is of use in solubilising smaller organic molecules. Examples of small organic molecules include glucose, carboxyfluorescin and many pharmaceutical agents, for example anti-cancer agents, but, of course, the process could equally be applied to other small organic molecules, for example vitamins or pharmaceutically or biologically active agents. In addition, compounds such as calcium chloride and sodium phosphate can also be solubilised using this process. Indeed, the present invention would be particularly advantageous for pharmaceutically and biologically active agents since the use of non aqueous solutions may enable the route by which the molecule enters the body to be varied, for example to increase bioavailability.

Another type of species which may be included in the hydrophobic compositions of the invention is an inorganic material such as a small inorganic molecule or a colloidal substance, for example a colloidal metal. The process of the present invention enables some of the properties of a colloidal metal such as colloidal gold, palladium, platinum or rhodium, to be retained even in hydrophobic solvents in which the particles would, under normal circumstances, aggregate. This could be particularly useful for catalysis of reactions carried out in organic solvents.

A process somewhat similar to that of the present invention is disclosed by Okahata et al (*J. Chem. Soc. Chem. Commun.*, 1988, 1392–1394). However, it seems that the array of protein surrounded by amphiphile molecules produced by the authors of that document differed considerably from that produced by the method of the present invention. In particular, the authors stated that the amphiphile molecules reacted with the protein in the liquid medium by hydrogen bonding or via an electrostatic interaction to form a solid precipitate. In contrast, it seems that in the present invention the hydrophilic species does not interact chemically with the amphiphile molecules in the liquid medium.

There are numerous amphiphiles which may be used in the present invention and zwitterionic amphiphiles such as phospholipids are among those which have been found to be especially suitable. Phospholipids having a phosphatidyl choline head group have been used with particular success and examples of such phospholipids include phosphatidyl choline (PC) itself, lyso-phosphatidyl choline (lyso-PC), sphingomyelin, derivatives of any of these, for example hexadecylphosphocholine or amphiphilic polymers containing phosphoryl choline. In the present application, the terms phosphatidyl choline (PC) and lecithin are used interchangeably. Suitable natural lecithins may be derived from any convenient source, for example egg and, in particular, soya. In most cases, it is preferable to select an amphiphile which is chemically similar to the chosen hydrophobic solvent and this is discussed in greater detail below.

The fact that the present inventors have found zwitterionic amphiphiles such as phospholipids to be particularly suitable for use in the process is a further indication of the significant differences between the present invention and the method of Okahata et al. Significantly, the authors of that prior art document concluded that anionic and zwitterionic lipids were completely unsuitable for use in their method and stated that they obtained zero yield of their complex using these lipids.

The hydrophobic solvent of choice will depend on the purpose for which the composition is intended, on the type of species to be solubilised and on the amphiphile. Suitable solvents include long chain fatty acids with unsaturated fatty acids such as oleic and linoleic acids being preferred, alcohols, particularly medium chain alcohols such as octanol and branched long chain alcohols such as phytol, monoglycerides such as glycerol monooleate (GMO), diglycerides and triglycerides, particularly medium chain triglycerides and mixtures thereof.

Optimum results are generally obtained when the hydrophobic solvent and the amphiphile are appropriately matched. For example, with a solvent such as oleic acid, lyso-PC is a more suitable choice of amphiphile than PC, whereas the converse is true when the hydrophobic solvent is a triglyceride.

In addition, in some cases it has been found to be advantageous to add a quantity of the amphiphile to the hydrophobic solvent before it is brought into contact with the hydrophilic species/amphiphile array. This ensures that the amphiphile molecules are not stripped away from their positions around the hydrophilic species because of the high affinity of the amphiphile for the hydrophobic solvent.

It is very much preferred that the preparations of the invention are optically clear and this can be monitored by measuring turbidity at visible wave lengths and, in some cases, by checking for sedimentation over a period of time.

A hydrophile/amphiphile array in which the hydrophilic head groups of an amphiphile are orientated towards a hydrophilic species has been produced before but it has never been suggested that this type of composition may be soluble in lipophilic solvents.

Kirby et al, in *Bio/Technology*, November 1984, 979–984 and in *Liposome Technology*, Volume I, pages 19–27, Gregoriadis, Ed., CRC Press, Inc., Boca Raton, Fla., USA describe a method for the preparation of liposomes in which a phospholipid is suspended in distilled water to form small unilamellar vesicles or multilamellar vesicles, mixed with the material to be entrapped and freeze dried. The mixture is then rehydrated to give liposomes.

At the time of publication of this prior art there was extensive worldwide interest in the preparation of liposomes but the idea of producing a single phase hydrophobic preparation of a macromolecule seems either never to have been thought of or to have been dismissed as impossible or of little value. Certainly, there is no suggestion in any of the prior art that the intermediate arrays could be put to any other use than the preparation of liposomes. Even if a single phase hydrophobic preparation had been a desirable objective, the idea of adding a hydrophobic rather than a hydrophilic solvent would have been unlikely to have been taken seriously because there was a strong prejudice in the art against hydrophobic preparations of hydrophilic molecules.

The orientation of amphiphile molecules into an array with their hydrophilic head groups facing the moieties of a hydrophilic species can be achieved in several ways and examples of particularly suitable methods are discussed in more detail below.

In a first method, which has a similar starting point to the method described by Kirby et al, supra, a hydrophilic species is mixed with a dispersion of an amphiphile in a hydrophilic solvent, such that the amphiphile molecules form an assembly in which the hydrophilic head groups face outwards towards the hydrophilic phase which contains the hydrophilic species. The hydrophilic solvent is then removed to leave a dry composition in which the hydrophilic head groups of the amphiphile molecules are orientated towards the hydrophilic species.

In the method described by Okahata et al, a solution of a protein was also mixed with a dispersion of an amphiphile in water. However, significantly, the authors of that paper believed that it was necessary to obtain a precipitate which would then be soluble in hydrophobic solvents. Since many of the preferred amphiphiles of the present invention do not form such a precipitate, Okahata et al concluded that they would be of no use. In the process of the present invention, no precipitate is required and, indeed, it is generally thought to be undesirable to allow the formation of a precipitate since this results in a reduced yield of the required product.

In this first method, it is preferred that the hydrophilic solvent is water although other polar solvents may be used.

The form taken by the amphiphile assembly may be micelles, unilamellar vesicles, preferably small unilamellar vesicles which are generally understood to have a diameter of about 25 nm, multilamellar vesicles or tubular structures, for example cochleate cylinders, hexagonal phase, cubic phase or myelin type structures. The form adopted will depend upon the amphiphile which is used and, for example, amphiphiles such as phosphatidyl choline (PC) tend to form small unilamellar vesicles whereas lyso-phosphatidyl choline forms micelles. However, in all of these structures, the hydrophobic tails of the amphiphile molecules face inwards towards the centre of the structure while the hydrophilic head groups face outwards towards the solvent in which the hydrophilic species is dispersed.

The weight ratio of amphiphile:hydrophilic species will generally be in the region of from 1:1 to 100:1, preferably from 2:1 to 20:1 and most preferably about 8:1 for PC and 4:1 for lyso-PC.

These ratios are preferred ratios only and, in particular, it should be pointed out that the upper limit is set by economic considerations which mean that it is preferable to use the minimum possible amount of amphiphile. The lower limit is somewhat more critical and it is likely that ratios of 2:1 or below would only be used in cases where the hydrophilic species has a significant hydrophobic portion or is exceptionally large.

Good performance is obtained when the solvent is removed quickly and a convenient method for the removal of the solvent is lyophilisation, although other methods can be used.

In some cases, it may be helpful to include salts in the hydrophilic solution, particularly if the hydrophilic species is a macromolecular compound such as a large protein. However, because the presence of larger amounts of inorganic salts tends to give rise to the formation of crystals and, hence, to a cloudy solution, it is preferred that organic salts are used rather than inorganic salts such as sodium chloride. Ammonium acetate is especially suitable for this purpose since it has the additional advantage that it is easily removed by freeze drying.

A second method for the preparation of a composition containing an array of amphiphiles with their head groups pointing towards the moieties of the hydrophilic species is to co-solubilise the hydrophilic species and the amphiphile in a common solvent followed by removal of the solvent.

This second method of forming the array is novel and itself forms a part of the invention.

Therefore, in a second aspect of the invention there is provided a process for forming a hydrophile/amphiphile array wherein the hydrophilic head groups of the amphiphile molecules are orientated towards the hydrophilic species, the process comprising co-solubilising a hydrophilic species and an amphiphile in a common solvent and subsequently removing the common solvent.

When this method is used, it is preferred that the weight ratio of amphiphile:hydrophilic species is from about 1:1 to 50:1, preferably from 2:1 to 10:1 and most preferably about 4:1.

The common solvent must, of course, dissolve both the amphiphile and the hydrophilic species and will, for preference, be a polar organic solvent such as dimethylformamide, dimethylsulphoxide or, most suitably, glacial acetic acid.

In this method, in contrast to the first method, it is unlikely that an array will be formed before the removal of the common solvent.

It seems probable that, on removal of the solvent, the amphiphile molecules tend to order themselves in sheets with their head groups towards the hydrophilic species and their lipophilic tail groups facing away from the hydrophilic species. However, the effectiveness of the present invention does not depend on the accuracy or otherwise of this observation.

It has been observed that good results are obtained when the solvent is removed slowly, for example by drying under a stream of nitrogen, probably because this allows more time for the amphiphile molecules to reorder themselves.

A third method for forming the hydrophile/amphiphile array comprises emulsifying a solution of the amphiphile in a hydrophobic solvent with a solution of the hydrophilic species in a hydrophilic solvent to give an emulsion, and removing the solvents.

The emulsion may be either a water-in-oil or an oil-in-water type, but if a small hydrophilic species is used rather than a macromolecule, then a water-in-oil emulsion may be more suitable.

Any hydrophobic solvent for the amphiphile may be used, but for the water-in-oil emulsions preferred for use with small hydrophilic species, a low boiling point solvent such as diethyl ether is preferred since it has been found that the best results are obtained when the hydrophobic solvent is removed slowly by gentle methods such as evaporation and, clearly, this is most effective using a low boiling point solvent. Low boiling point solvents are also preferred for water-in-oil emulsions although, for these, lyophilisation is a more suitable method of solvent removal. The hydrophilic solvent will preferably be aqueous.

The weight ratio of amphiphile:hydrophilic species may be from about 1:1 to 50:1, preferably from 2:1 to 10:1 and most preferably about 4:1.

The ratio of hydrophilic solution to hydrophobic solution is not critical, but if small hydrophilic species are used, it is preferably such as to ensure the formation of a water-in-oil emulsion rather than an oil-in-water emulsion.

When a water-in-oil emulsion is formed, the third method is suitable for use with any type of hydrophilic species but the first and second methods have been found to be less suited to use with small molecules than the third method.

An alternative method of forming the array, which may be particularly suited to use with small hydrophilic species, is to entrap the hydrophilic species in closed lipid vesicles such as small unilamellar vesicles (SUVs) dispersed in a hydrophilic solvent and then to remove the solvent.

The product of the process of the invention is new since it makes possible the production of single phase hydrophobic preparations comprising a hydrophilic species which would not normally be soluble in a hydrophobic solvent. Therefore, in a third aspect of the invention there is provided a single phase hydrophobic preparation comprising a hydrophilic species in a hydrophobic solvent obtainable by the process of the invention.

Additionally, the present invention also provides a single phase hydrophobic preparation comprising a hydrophilic species and an amphiphile in a hydrophobic solvent, characterised in that the moieties of the hydrophilic species are surrounded by amphiphile molecules with the hydrophilic head groups of the amphiphile molecules orientated towards the hydrophilic species.

Preferred hydrophilic species, amphiphiles and hydrophobic solvents are as specified for the process just described.

It may also be desirable to include other constituents in the single phase hydrophobic preparation in addition to the hydrophilic species. This is often particularly appropriate when the hydrophilic species is a macromolecule and, in that case, the preparation may include, for example, bile salts, vitamins or other small molecules which bind to or are otherwise associated with the macromolecules.

Although some macromolecule/amphiphile arrays were disclosed by Kirby et al, supra, the arrays disclosed were all intermediates in the formation of liposomes and, as discussed above, there has been no previous interest in non-liposomal or hydrophobic compositions comprising this type of entity. Therefore, the arrays of the present invention in which the amphiphile is one which does not form small unilamellar vesicles and would therefore not be expected to form liposomes are new.

In a further aspect of the invention there is provided an array of amphiphile molecules and hydrophilic species characterised in that the hydrophilic head groups of the amphiphile molecules are orientated towards the hydrophilic species and wherein there is no chemical interaction between the amphiphile and the hydrophilic species, provided that the amphiphile is one which is not capable of forming liposomes when water is added to the array.

One example of an amphiphile which is not capable of forming liposomes is lyso-lecithin. In most aqueous environments, this amphiphile forms micelles rather than small unilamellar vesicles and it is therefore unsuitable for use in the preparation of liposomes. It is however extremely useful in the process of the present invention, particularly when used in conjunction with a compatible hydrophobic solvent such as oleic acid.

One advantage of the preparations of the present invention is that they are essentially anhydrous and therefore stable to hydrolysis. They are also stable to freeze-thawing and have greater stability at high temperatures, probably because water must be present in order for the protein to unfold and become denatured. This means that they may be expected to have a much longer shelf life than aqueous preparations of the hydrophilic species.

The solutions of the present invention are extremely versatile and have many applications. They may either be used alone or they may be combined with an aqueous phase to form an emulsion or similar two phase composition which forms yet a further aspect of the invention.

In this aspect of the invention there is provided a two phase composition comprising a hydrophilic phase and a hydrophobic phase, the hydrophobic phase comprising a preparation of a hydrophilic species in a lipophilic solvent obtainable by a process as described herein.

Generally, in this type of composition, the hydrophobic phase will be dispersed in the hydrophilic phase.

It is surprising that a stable two phase composition of this type can be formed since it might have been expected that the hydrophilic species would not remain in the hydrophobic phase but would, instead, pass to the hydrophilic phase. However, it has been demonstrated that in many cases this does not occur and that the hydrophilic species does, indeed, remain in association with the dispersed hydrophobic phase and is not present in free solution. It is possible that this is a result of some residual water or other hydrophilic remaining bound to the hydrophilic head group of the amphiphilic molecule. One advantage of this is that osmotic leakage of the hydrophilic species is not a problem in the compositions of the invention as is the case with some known systems, particularly liposomal systems.

The two phase compositions may be emulsions which may either be transient or stable, depending on the purpose for which they are required.

The average size of the emulsion particles will depend on the exact nature of both the hydrophobic and the aqueous phases. However, it may be in the region of 2 $\mu$m Dispersion of the hydrophobic preparation in the aqueous phase can be achieved by mixing, for example either by vigourous vortexing for a short time for example about 10 to 60 seconds, usually about 15 seconds, or by gentle mixing for several hours, for example using an orbital shaker.

Emulsions containing the hydrophobic preparations of the invention can also be used in the preparation of microcapsules. If the emulsion is formed from a gelatin-containing aqueous phase, the gelatin can be precipitated from the solution by coacervation by known methods and will form a film around the droplets of the hydrophile-containing hydrophobic phase. On removal of the hydrophilic phase, microcapsules will remain. This technology is known in the art, but has proved particularly useful in combination with the preparations of the present invention.

One way in which the compositions of the present invention may be used is for the oral delivery to mammals, including man, of substances which would not, under normal circumstances, be soluble in lipophilic solvents. This may be of use for the delivery of dietary supplements such as vitamins or for the delivery of biologically active substances, particularly proteins or glycoproteins, including insulin and growth hormones.

In a further application, it is possible to encapsulate or microencapsulate, for example by the method described above, nutrients such as vitamins which can then be used, not only as human food supplements but also in agriculture and aquaculture, one example of the latter being in the production of a food stuff for the culture of larval shrimps.

In addition, the compositions find application in the preparation of pharmaceutical or other formulations for parenteral administration, as well as formulations for topical or ophthalmic use. For this application, it is often preferable to use an emulsion of the oil solution and an aqueous phase as described above.

Many therapeutic and prophylactic treatments are intended for sustained or delayed release or involve a two component system, for example including a component for immediate release together with a component for delayed or sustained release. Because of their high stability, the preparations of the invention are particularly useful for the formulation of a macromolecule intended for sustained or delayed release.

The longer shelf life of the compositions of the present invention is a particular advantage in the pharmaceutical area.

The hydrophile-in-oil preparations may find application in the pharmaceutical or similar industries for flavour masking. This is a particular problem in the pharmaceutical industry since many drugs have unpleasant flavours and are thus unpopular with patients, especially children.

A further use is in the cosmetics industry where, again, hydrophobic preparations of hydrophilic compounds can very easily be incorporated into a cosmetic formulation. Examples of macromolecules which may be used in this way include those with moisturising or enzymatic action of some sort. The invention can also be used for the incorporation of proteins such as collagen into dermatological creams and lotions.

Finally, the invention has numerous uses in the field of chemical and biological synthesis, for example, non-aqueous enzymatic synthesis.

The invention will now be further described with reference to the following examples.

EXAMPLE 1

Salmon calcitonin was solubilised in an oil phase as follows. All chemicals used in this and other examples were of analytical or chemical grade.

Purified egg phosphatidyl choline dissolved in chloroform/methanol, 2:1 (v/v) was rotary evaporated to form a dry film and distilled water added to give a lipid concentration of 100 mg/ml. After flushing thoroughly with nitrogen, the lipid was dispersed by vigorous vortexing, followed by probe sonication for a total period of five minutes, until an opalescent dispersion of small unilamellar vesicles (SUVs) was obtained. Throughout the sonication step, the vessel was immersed in an ice slurry bath, and sonication carried out in 30 second bursts, interspersed with 30 second cooling intervals. The suspension of SUVs was centrifuged at 1000×g for 10 minutes to pellet aggregated lipid, and the supernatant was decanted and diluted two-fold in distilled water to give a concentration of 50 mg of lipid per ml.

A solution of salmon calcitonin was prepared by dissolving 5 mg of the protein to 1 ml of distilled water, to give a clear solution. Equal volumes (0.5 ml) of protein solution and lipid dispersion were added together in a 10 ml round-bottomed test tube, and mixed well. The resultant mixture was shell-frozen in liquid nitrogen, and lyophilised overnight under a vacuum of less than 0.1 mbar and a condenser temperature of −45° C.

The following day, 300 mg of oleic acid BP was added to the lyophilisate, and mixed gently to bring all the dry solid into contact with the oil. The mixture was allowed to stand at room temperature for a period of about one to two hours, with occasional mixing, during which time all the solid was taken into the oil to form a single clear lipid phase, which was optically transparent.

EXAMPLE 2

Soy phosphatidyl choline SUVs at a concentration of 100 mg/ml, were prepared by vortexing dry lipid in distilled water and then sonicating as in Example 1. An aqueous solution of salmon calcitonin was prepared at 10 mg/ml, and an aliquot of 0.8 g was transferred to a test tube. 1 g of SUVs was added, and the contents shell frozen and freeze-dried overnight. 1.2 g of 95% oleic acid was added to the lyophilate and dispersion carried out as in Example 1. The calcitonin preparation, which contained 6.7 mg protein/g oleic acid, was completely clear.

EXAMPLE 3

An aprotinin-containing lyophilate was prepared under the same conditions as described for salmon calcitonin in Example 2 above, and then stored for 5 days at 4° C., in a desiccator together with phosphorus pentoxide, in conditions under which essentially all water, whether bound or free, would be expected to be removed. Subsequent dispersion in oleic acid was not impaired, since addition of 300 mg of oleic acid gave an optically clear oil phase.

EXAMPLE 4

Soy phosphatidyl choline SUVs at 100 mg/ml in distilled water were prepared as in Example 2. Salmon calcitonin solution at 20 mg/ml was prepared by dissolving 31.8 mg in 1.59 g with distilled water and 0.67 g of the clear solution (13.4 mg of protein) was mixed with 1.0 g SUVs (100 mg of PC) in a test-tube. The mixture was shell-frozen, freeze-dried and then dispersed in oleic acid as in example 1 (but using 200 mg oleic acid). The resulting clear oil phase contained 42.7 mg calcitonin/g.

EXAMPLE 5

Egg PC SUVs at a concentration of 100 mg PC/ml were prepared as in Example 1. An insulin solution at 10 mg/ml was made by preparing an aqueous suspension at a slightly higher concentration, adding glacial acetic acid at a rate of 20 mg/g of insulin used, and then adding sufficient water to give the desired insulin concentration. After mixing and standing for 15 minutes, a clear solution was formed. To 1.25 ml of SUVs in a test-tube, were added 1.25 ml of insulin solution, and the mixture shell-frozen and freeze-dried overnight. The following day, 0.252 g of oleic acid was added and the tube vortexed to completely "wet" the lyophilate. The preparation was left overnight for complete dispersion to occur, after which it had the appearance of a yellow, optically clear dispersion displaying strong opalescence. After 7 weeks storage under nitrogen in a sealed tube, at room temperature, there was no apparent change in the appearance (eg sedimentation) of the DPLC preparation.

EXAMPLE 6

SUVs were prepared as in Example 2 using 100 mg of soy phosphatidyl choline per g, and insulin solution prepared as in Example 2. 50 mg of SUVs (5 mg of PC) and 47 mg of insulin solution (0.47 mg protein) were added to a small glass vial, frozen, freeze-dried and dispersed in 100 mg of diolein. The initial granular dispersion became clear after 2 hours.

EXAMPLE 7

95% pure egg phosphatidyl choline, provided in a dry form, was dispersed directly in distilled water by vortexing, to give a suspension of multilamellar vesicles with a phospholipid concentration of 100 mg/g. The material was extruded 3 times at a pressure of 20,000 psi through an EmulsiFlex™ apparatus, following the manufacturer's instructions. The resulting opalescent dispersion was diluted to 50 mg/ml with distilled water, flushed with nitrogen and stored at 4° C. until needed. 30 mg of salmon calcitonin, together with 30 mg of aprotinin, were dissolved together in 6 ml distilled water and then mixed with 39.6 ml of the phospholipid dispersion prepared above. The mixture was dispensed into appropriately-sized aliquots, shell frozen, freeze-dried and then a total of 47.52 g of glycerol monooleate BP (melted by warming to 40° C.) added, mixing as described in example 1 to produce an optically clear opalescent dispersion of DPLC.

EXAMPLE 8

Synthetic dipalmityl phosphatidyl choline was dissolved in a solvent mixture of chloroform/methanol, 2:1 (v/v) and then rotary evaporated to form a thin film. The dried lipid was dispersed in distilled water at a concentration of 30 mg/ml and sonicated to form an opalescent dispersion of SUVs. The procedure was generally similar to Example 1, except that the temperature was maintained at about 45° C., ie above the transition temperature of the lipid. A solution of insulin at 10 mg/ml was prepared as in Example 4, and 0.14 ml aliquots (1.4 mg of protein) were transferred to small tubes, together with 0.5 g aliquots of SUVs (15 mg of DPPC). The mixtures were shell frozen and freeze-dried, and the resulting lyophilates dispersed in 300 mg of oleic acid to give clear "solutions" of protein. Comparative experiments showed that it was not necessary to work above the transition temperature when dispersing the lyophilates.

EXAMPLE 9

A micellar solution of egg lysophosphatidyl choline in water was prepared at a concentration of 36 mg/ml, and 0.137 ml transferred to a small tube. A solution of insulin at 10 mg/ml was prepared as in Example 4 and 0.137 ml transferred to the above tube. The tube contents were shell frozen, freeze-dried and then mixed with 0.3 g of oleic acid, to produce a clear dispersion containing 4.6 mg insulin/g of oleic acid, having an absorbance of 0.023 at 600 nm.

EXAMPLE 10

Soy phosphatidyl choline SUVs at 100 mg/ml were prepared as in Example 2 and insulin solution containing 10 mg/ml, was prepared as in Example 4. Into each of 5 tubes was added 0.1 ml of insulin solution (1 mg of protein), and 0.3 mg of SUVs (30 mg of PC), and the mixtures were shell-frozen and freeze-dried overnight. The resulting lyophilates were each dispersed in 300 mg of one of a series of fractionated coconut oil, viz. Miglyols 810, 812, 818, 829 and 840. (The word Miglyol is a trade mark). All preparations except that to which Miglyol 829 had been added, dispersed rapidly to form opalescent "solutions", while the latter formed a thick, opaque gel. The dispersions became clearer on standing so that by the following day, Miglyols 812, 818, and 840 were completely clear and Miglyol 810 was slightly opalescent. Miglyol 829 remained as a turbid gel.

EXAMPLE 11

Soy phosphatidyl choline SUVs were prepared as in Example 2, and salmon calcitonin solution was prepared at 10 mg/ml. 100 uL of calcitonin solution (1 mg of protein) and 300 mg of SUVs (30 mg of PC) were added to each of 6 small test-tubes, and the contents shell frozen and freeze-dried. To each of 5 of the lyophilates was added 300 mg of Miglyol 810, 812, 818, 829 or 840, while 300 mg of medium chain triglyceride oil (MCT) oil was added to the sixth. After mixing, all preparations were opalescent or turbid but became clearer on standing. By the following morning, the dispersions in Miglyol 810 and 840 were turbid, those in MCT oil and Miglyol 812 were opalescent and those in Miglyols 818 and 829 were completely clear. On warming gently, the opalescent and turbid dispersions became clear, but reverted to their previous form after standing overnight at room temperature.

EXAMPLE 12

An aqueous solution of Candida cylindericae lipase at 10 mg/g was prepared, together with a preparation of soy phosphatidyl choline SUVs at 100 mg/ml (see Example 2). 50 μL aliquots of lipase solution (0.5 mg of protein) were added to several small test-tubes and 100 uL of SUVs (10 mg of PC) added to each. The mixtures were immediately frozen, freeze-dried, flushed with nitrogen and then sealed with parafilm before storing in the freezer. One of the lyophilates was thawed and mixed with 0.44 g of linoleic acid, forming a completely clear dispersion of DPLC after 30 minutes. 0.1 g of cholesterol was dissolved in the oil and the tube flushed with nitrogen, sealed with parafilm and transferred to a 37° C. incubator. After 2 days, the mixture was analysed by reverse-phase thin layer chromatography and showed, in addition to the initial reactants, a spot of identical Rf value to a standard of cholesterol linoleate. This indicates that the enzyme solubilized within the oil phase is catalytically active. This synthetic esterification reaction is in contrast to the normal hydrolytic processes usually associated with lipase action.

EXAMPLE 13

Soy phosphatidyl choline SUVs at 100 mg/ml were prepared as in Example 2. Two 0.15 ml aliquots (15 mg of PC) were dispensed into small test-tubes and 0.33 g of an aqueous solution of mushroom tyrosinase at 3 mg/ml, was added to each. The contents were shell frozen and freeze-dried. To one lyophilate was added 0.3 g of oleic acid, and to the other, 0.3 g of MCT oil, after which the tubes were mixed by vortexing. The MCT preparation formed a clear brown dispersion after 45 minutes while the oleic acid one took 2 hours.

The dispersions were tested against 2 separate substrates for the enzyme, catechol and tyrosine, and the results compared with those obtained with an aqueous solution of free enzyme. Each reaction was carried out in the presence of proline. When free enzyme was used, each substrate was gradually converted to an intensely coloured pigment. However, in the presence of the DPLC dispersions, pigment formation occurred with catechol but not with tyrosine. Colour intensity was less with the oleic acid preparation than with MCT oil, possibly due to an effect of low pH on enzyme activity. The same pattern of substrate conversion was seen when the oil phases were temporarily emulsified within the aqueous phase by vortexing. However, when emulsification was carried out in the presence of Triton X100™, pigment formation occurred with both substrates.

The proposed explanation for the observed behaviour is that catechol is able to partition into the oil and gain access to the encapsulated enzyme, whereas tyrosine is confined to the aqueous phase. The quinone product of enzyme action on catechol can then partition back into the aqueous phase and interact with proline to form a coloured product. This experiment demonstrates that the enzyme is encapsulated in an active form within the oil, and is not released into the aqueous phase during dispersion. However, when a surface active agent such as Triton X100™ is added, the enzyme is released and free to act on either substrate.

EXAMPLE 14

Colloidal gold, of mean particle diameter 30 nm, was prepared and stabilised by adding bovine albumin to 0.001%. 0.2 g of the wine red gold sol was weighed into a small tube together with 0.2 g of egg phosphatidyl choline SUVs at a concentration of 100 mg/ml, prepared as in Example 1. The mixture was shell frozen, freeze-dried and then mixed with 0.3 g of oleic acid. After about 2 hours, with occasional shaking, the dispersion had cleared completely to form a red coloured oil phase which closely resembled the original aqueous gold sol.

EXAMPLE 15

1 mg of the peptide antibiotic, Nisin, was mixed with 0.2 g of the same egg phosphatidyl choline SUVs used for Example 14, and treated in similar fashion. A crystal clear dispersion had formed within 2 hours.

EXAMPLE 16

Tyrosinase was incorporated into oleic acid as described in Example 13. One part (by weight) of this dispersion was added to four parts of 20% aqueous gelatine warmed to 50° C., mixed rapidly by vortexing, and then transferred to a small beaker where mixing was continued using a magnetic stirrer. Two parts of 20% aqueous sodium sulphate were added dropwise and uniformly, and the mixture was then poured into 40 parts of 7% aqueous gelatine at 15° C. while the latter was being magnetically stirred. Mixing was continued for a further minute and then a portion of the resulting gelatine microcapsules were tested for enzyme activity using catechol and tyrosine as substrates. As seen in Example 13, colour formation occurred with catechol but not with tyrosine, indicating that the enzyme/lipid complexes had remained intact within the oil phase during microencapsulation of the oil.

EXAMPLE 17

10 mg of cytochrome C, haemoglobin and FITC-dextran were each dissolved in 1 ml of distilled water. 4.4 mg of RNA (extracted from Torula yeast) was dissolved in 1 ml of phosphate-buffered saline. 2×50 $\mu$l of each of these solution was dispensed into fresh glass tubes, and to one of each of these sets of solutions was added 250 $\mu$l of SUVs prepared as in example 1 at a concentration of 40 mg/ml of egg yolk lecithin (PC).

Both sets of tubes were shell-frozen and lyophilised overnight as above. The following day 300 $\mu$l of oleic acid was added to each of the tubes. The samples were left to stand at room temperature with occasional vortexing for one hour until complete dispersion had been achieved. The oils were allowed to stand overnight. The turbidity of the samples prepared without PC was greater than those containing PC.

The following day, sediments had settled out in the samples prepared without PC. Without disturbing any of the samples, the top 150 $\mu$l of each sample was taken off, and the absorbances measured of both the material removed, and the material left behind, after mixing; comparison of the two readings allowed one to calculate the percentage sedimentation for samples with and without PC (error in measurements ±5%) Values obtained are listed below.

| | Percent sedimentation after 24 hours | |
|---|---|---|
| Macromolecule | +PC | −PC |
| Cytochrome C | 3.1 | 76 |
| Haemoglobin | 0 | 44 |
| FITC dextran | 0 | 68 |
| RNA | 0 | 73 |

EXAMPLE 18

Procedure as in Example 1, except that protein solutions consisted of ferritin or horseradish peroxidase (HRPO) at a concentration of 10 mg/ml in ammonium acetate (10 mg/ml), and the SUVS were composed of egg yolk phosphatidyl choline at a concentration of 50 mg/ml) in ammonium acetate (also 10 mg/ml). After lyophilising and dispersing in oleic acid, optically clear solutions were obtained (although ferritin solution showed some opalescence, and was strongly coloured)

The HRPO solution was divided into two -equal portions, and one portion was put through five freeze-thaw cycles by cooling repeatedly to +4° C., solidifying the oleic acid each time, before bringing it back to room temperature. No difference in optical clarity was observed between samples freeze-thawed, and samples left untouched.

EXAMPLE 19

In the following procedure, a different method was employed to solubilise insulin in oil phase from that described above. The preparation was performed several times in parallel using different quantities of phosphatidyl choline (PC).

100 mg of insulin were dissolved in 2 ml of glacial acetic acid with vortexing. 500 mg of PC were dissolved in 5 ml of glacial acetic acid with vortexing. Into each of five glass 2 ml screw-capped vials, 100 $\mu$l of the insulin solution were dispensed. Different volumes (100, 200, 300, 400, 500 $\mu$l) of PC solution were dispensed into each of these vials, and the contents of each mixed well.

The solutions were evaporated to dryness under a stream of nitrogen with vortexing, then the last remnants of solvent were removed at room temperature under vacuum ($8\times10^{-2}$ mbars) in a lyophiliser overnight. The following day 300 $\mu$l of oleic acid was added to each vial, and the contents of the vials mixed gently on an orbital shaker for a further 24 hours.

Absorbances of 150 $\mu$l each of the solutions were measured at 450 nm, using an automated plate reader. The results were as follows:

| Tube number | 1 | 2 | 3 | 4 | 5 |
|---|---|---|---|---|---|
| Insulin (mg) | 5 | 5 | 5 | 5 | 5 |
| Oleic acid (mg) | 300 | 300 | 300 | 300 | 300 |
| PC (mg) | 50 | 40 | 30 | 20 | 10 |
| PC:Insulin ratio | 10:1 | 8:1 | 6:1 | 4:1 | 2:1 |
| OD$_{450}$ | 0.123 | 0.124 | 0.116 | 0.115 | 0.714 |

All the solutions obtained appeared optically clear, except for #5, which was turbid and scattered light strongly.

EXAMPLE 20

The same procedure employed as described in Example 19, except that bovine brain sphingomyelin was used instead of phosphatidyl choline, resulting in proportions by weight of insulin/sphingomyelin/oleic acid of 5/50/200. A completely clear solution was obtained after mixing the dried solids with the oil for one hour. On leaving to stand at room temperature for several days, a solid opaque gel was formed, which gave a clear solution again on warming to 37° C.

EXAMPLE 21

Procedure as in Example 1, except that protein solutions consisted of horseradish peroxidase (HRPO) at a concentration of 10 mg/ml in distilled water, and the SUVS were composed of egg yolk phosphatidyl choline and prepared using the Emulsiflex™ method described in Example 7 at a concentration of 50 mg/ml. After lyophilising, the solid material was dispersed in either phytol or glycerol mono-oleate. Optically clear solutions were obtained in each case.

EXAMPLE 22

Wheat germ tRNA was dissolved in distilled water at a concentration of 5 mg/ml, and 50 µl aliquots of the solution were mixed with 100 µl or 50 µl of SUVs composed of soya PC at a concentration of 50 mg/ml in distilled water. The ratios of PC to tRNA were 20:1 and 10:1 respectively. The mixtures were frozen at –20° C. and lyophilised to give a dry white cake. Addition of 100 µl of oleic acid, followed by gentle mixing on an orbital shaker, gave an optically clear solution for the 20:1 PC:RNA ratio, in contrast to 10:1 PC:RNA, or tRNA in the absence of PC, which gave turbid suspensions which were optically opaque, as demonstrated by OD readings at 650 nm.

| PC:RNA ratio | 20:1 | 10:1 | 0 |
|---|---|---|---|
| OD$_{450}$ | 0.044 | 0.240 | 0.657 |

EXAMPLE 23

Aprotinin was dissolved in distilled water at a concentration of 10 mg/ml. Hexadecyl phosphocholine (HDPoC) was dissolved in distilled water at a concentration of 100 mg/ml. To aliquots of 100 µl of aprotinin solution, volumes of HDPOC were added ranging from 0 through to 10, 20, 30, 40 to 50 µl. The mixtures were frozen at –20° C. and lyophilised overnight. The following day 100 µl of oleic acid was added to each sample and shaken for one hour at room temperature on an orbital shaker. Optically clear solutions were obtained at lipid:protein ratios of 4:1 and 5:1, as demonstrated by OD readings at 650 nm.

| Lipid:protein ratio | 0 | 1:1 | 2:1 | 3:1 | 4:1 | 5:1 |
|---|---|---|---|---|---|---|
| OD$_{650}$ | 1.117 | 0.869 | 0.438 | 0.207 | 0.094 | 0.099 |

EXAMPLE 24

4 mg of peroxidase was dissolved in 4 ml of distilled water, and 100 µl aliquots were dispensed into glass screw-capped 2 ml vials. 100 µl sonicated DMPC (dimyristoyl phosphatidyl choline, 100 mg/ml in distilled water) was added to each vial, mixed well and lyophilised.

When the mixture was completely dry, the protein/lipid complex was dispersed by addition to each vial of 100 µl of tertiary butanol, either alone or containing OPD (ortho-phenylene diamine) in solution at a concentration of 3 mg/10 ml. Controls were prepared by adding t-butanol ±OPD to tubes either empty, or containing DMPC in the absence of enzyme. Duplicates of each combination were prepared, and to one set of tubes 10 µl of cumene hydroxide substrate was added with mixing. After leaving to stand at room temperature for half an hour, the optical density of each sample was read at 450 nm in a microplate reader. Results obtained after background subtraction are presented in the table.

|  | Enzyme/DMPC | DMPC alone | Solvent alone |
|---|---|---|---|
| OPD alone | 0.249 | 0.032 | 0.015 |
| OPD + Cumene Hydroperoxide | 2.517 | 0.075 | 0.051 |

EXAMPLE 25

Octyl glucoside was dissolved in distilled water and dispensed into wells of a microplate to give the following amounts of amphiphile per well: –0, 0.5, 1.0, 1.5, 2.0, 2.5, 5, 7.5 and 10 mg. Aprotinin was dissolved in distilled water at a concentration of 5 mg/ml, and 100 µl was dispensed into each well above, containing 0.5 mg of protein. The plate was mixed well, frozen at –20° C. and lyophilised overnight. The following day, 1000 µl of oleic acid was added to each well. The plate was shaken at room temperature, and optical density measurements at 550 nm taken at intervals with a plate reader. A low absorbance value indicates a low level of scattering, and corresponds to effective dispersion of protein in oil.

Employing the method described above, the effect of addition of octyl glucoside to act as an amphiphile to aid in dispersion of aprotinin in oleic acid is demonstrated. The results, expressed in terms of optical density as a function of octyl glucoside concentration (at constant protein concentration) at different times after addition of oleic acid are given in the table and accompanying graph.

| Octyl Glucoside (mg/well) | 1 hr | 4 hr | 8 hr |
|---|---|---|---|
| 0.00 | 0.548 | 0.458 | 0.489 |
| 0.50 | 0.082 | 0.043 | 0.103 |
| 1.00 | –0.003 | –0.008 | –0.008 |

-continued

| Octyl Glucoside (mg/well) | 1 hr | 4 hr | 8 hr |
|---|---|---|---|
| 1.50 | −0.004 | −0.015 | −0.015 |
| 2.00 | −0.007 | −0.012 | −0.013 |
| 2.50 | 0.006 | −0.004 | −0.002 |
| 5.00 | 0.307 | −0.013 | −0.014 |
| 7.50 | 0.65 | −0.015 | −0.014 |
| 10.00 | 1.628 | 0.817 | −0.014 |

EXAMPLE 26

10 mg of melanin were added to 1 ml of distilled water, and dissolved after raising pH with ammonium hydroxide solution. 50 ul of this concentrated solution was diluted 20-fold by addition to 950 ul of distilled water. To two rows of seven wells of a microplate 0, 12.5, 25, 37.5, and 50 ul of the dilute solution were added, and 12.5 and 25 ul of the concentrated solution. To each well of one row was added 100 ul of a soya phosphatidyl choline dispersion prepared by sonication for ten minutes with cooling at a concentration of 100 mg/ml. The other row was left untouched, the plate was mixed well, frozen at −20° C. and lyophilised overnight. The following day, 100 ul of M818 were added to wells in the row containing melanin/lipid complex, and 100 ul of distilled water was added to the wells in the row containing melanin alone. After all the solutions, which were red-brown in colour, became completely clear, optical densities at 600 nm were measured for all concentrations of melanin. It will be seen from the table and accompanying graph that Beer-Lambert's law is obeyed over this concentration range (ie the response curve is linear), and that the behaviour of melanin is identical for both oil and aqueous solutions. Melanin dispersed in M818 by sonication in the absence of phosphatidyl choline gave a black dispersion, which sedimented out after centrifugation giving a clear supernatant. No such changes were observed after centrifugation of the melanin/lipid complex dispersed in M818.

| Measurement at 600 nm Concn (mg/ml) | Miglyol | Water |
|---|---|---|
| 0 | 0 | 0 |
| 0.0625 | 0.078 | 0.072 |
| 0.125 | 0.157 | 0.159 |
| 0.187 | 0.23 | 0.23 |
| 0.25 | 0.306 | 0.333 |
| 1.25 | 1.565 | 1.259 |
| 2.5 | 2.857 | 2.653 |

EXAMPLE 27

A dispersion of soya phosphatidyl choline was prepared by probe sonication for ten minutes at a concentration of 100 mg/ml in distilled water with cooling. One millilitre of this suspension was dispensed into a glass vessel and 660 $\mu$l of a solution of Neomycin sulphate (5 mg/ml in distilled water) was added. After mixing, the contents of the tube were shell-frozen in liquid nitrogen, and lyophilised overnight. The following day, 1 g of Miglyol 818 was added, the vessel was flushed with nitrogen, sealed well and allowed to stand at room temperature overnight. An optically clear solution was obtained.

EXAMPLE 28

The same procedure was used as for Example 27, except that vasopressin was substituted for Neomycin sulphate.

EXAMPLE 29

The same procedure was used as for Example 27, except that 5-Fluorouracil was substituted for Neomycin sulphate.

EXAMPLE 30

The same procedure was used as for Example 27, except that 5-Fluoro deoxyuridine was substituted for Neomycin sulphate.

EXAMPLE 31

0.55 ml of ribonuclease solution (containing 10 mg RNAse/ml), was mixed with 1.6 ml of soy PC SUV prepared as in Example 2, shell-frozen in liquid nitrogen and freeze-dried overnight. The lyophilate was mixed with 1.6 g of Miglyol 818, vortexed and left to stand. After several hours a clear dispersion was formed.

EXAMPLE 32

To 32 $\mu$g of plasmid DNA in 40 $\mu$l of aqueous solution was added 40 $\mu$l of 0.2 mM spermine solution; the preparation was mixed and allowed to stand for 15 minutes for DNA condensation to occur. Soy PC SUVs were prepared as in Example 2, but containing 50 mg of PC/g, and 40 $\mu$l was added to the DNA/spermine mixture. The preparation was frozen, freeze-dried overnight and 100 $\mu$l of Miglyol 818 added to the resulting lyophilate. The preparation dispersed over a period of 1 hour to give a clear dispersion.

EXAMPLE 33

Two rows of 3 small test tubes were set up. To each tube in the first row was added 57 $\mu$l of a solution containing 10 mg insulin/ml, prepared as in Example 5. To each tube in the second row was added 0.2 ml of 0.267 mM carboxyfluorescein (CF). Soy PC SUV containing 100 mg PC/ml were prepared as in Example 2 and 0.2 ml added to every tube. The tube contents were mixed, shell-frozen and freeze-dried overnight. Melts of the high melting point triglycerides tripalmitin (TP) triheptadecanoin (TH) and tristearin (TS), each containing 2% (wt/wt) oleic acid, were prepared by adding the appropriate components together, heating to 78 C until liquifaction occurred and then briefly vortexing. The lyophilates were heated to the same temperature in an oven. To tubes 1, 2 and 3 of the insulin-containing lyophilates were added 150 mg of the TP, TH and TS-containing melts respectively. To tubes 1, 2 and 3 of the CF-containing lyophilates were added 10 mg of melts in the same order. After each addition, the tubes were capped, vortexed briefly and then returned to the oven. After several minutes, all of the CF dispersions were completely clear. The insulin preparations cleared over a period of 1 to 2 hours to form almost clear dispersions.

EXAMPLE 34

A series of lyophilates were prepared, each containing 0.3 mg glucose (derived from a solution containing 1.5 mg/ml) and 6 mg of soy PC (derived from SUV prepared as in Example 2. To 3 lyophilates were added 300 mg of octanol, oleic acid and Miglyol 818 respectively. The octanol preparation dispersed over a few minutes and the oleic acid and Miglyol preparations over 2 to 3 hours,to form clear dispersions.

EXAMPLE 35

Lyophilates were prepared derived from 0.8 ml of 25 mM calcium chloride together with 0.8 ml of soy PC SUV (prepared as in Example 2). To one was added 500 mg of Miglyol 818, and to the other, 500 mg of oleic acid. The oleic acid preparation formed a completely clear dispersion after several hours, and the Miglyol preparation after standing overnight.

EXAMPLE 36

To separate small glass vials were added 1 mg of aprotinin and 1 mg of insulin, each in the form of 100 μl of a solution containing 10 mg/ml. The insulin solution was prepared as in Example 5. To each vial was then added 0.2 ml of AOT (supplied as a 10% (w/v) solution in water. The mixtures were shell-frozen, lyophilized overnight, and 200 mg octanol added to each. The aprotinin preparation cleared rapidly but after 24 hours had formed an opalescent dispersion. The insulin preparation dispersed more slowly but was clear after standing overnight.

EXAMPLE 37

20 μl of lipase solution containing 0.8 mg of *Mucor mehii* lipase was added to each of 2 small glass vials. To one vial was added 89 μl of a micellar solution containing 36 mg lysoPC/ml, and to the other, 96 μl of soy PC SUV prepared as in Example 2. The contents of each vial were mixed, frozen in liquid nitrogen and freeze-dried overnight. To each lyophilate was added 500 mg of linoleic acid containing 88 mg cholesterol/g and 1 mg α-tocopherol/g. The vials were flushed with nitrogen, sealed and transferred to a roller mixer for 2 hours, by which time each had formed a clear dispersion. The vials were then incubated at 50 C overnight in a heating block. The mixtures, together with appropriate controls, were analysed by thin-layer chromatography and cholesterol linoleate was found to have been biosynthesised in each preparation.

It can therefore be seen that the present invention provides a method of incorporating a hydrophilic species into a lipophilic solution and a versatile product which has many different applications.

What is claimed is:

1. A process for the preparation of an essentially anhydrous optically clear hydrophobic preparation comprising a hydrophilic species in a hydrophobic solvent, the process comprising:
    (i) mixing a hydrophilic species with a dispersion consisting essentially of small unilamellar vesicles (SUVs) of an amphiphile in a hydrophilic solvent;
    (ii) removing the hydrophilic solvent to leave an array of amphiphile molecules with their hydrophilic head groups orientated towards the hydrophilic species and wherein there is no chemical interaction between the amphiphile and the hydrophilic species; and
    (iii) providing a hydrophobic solvent around the hydrophilic species/amphiphile array.
2. The process as claimed in claim 1, wherein the hydrophilic species is selected from the group consisting of macromolecules, supramolecular assemblies of macromolecules, small organic or inorganic molecules and colloidal substances.
3. The process as claimed in claim 2, wherein the macromolecule is selected from the group consisting of proteins, glycoproteins, oligo- or polynucleic acids, polysaccharides and supramolecular assemblies of any of these.
4. The process as claimed in claim 2, wherein the protein is selected from the group consisting of insulin, calcitonin, hemoglobin, cytochrome C, horseradish peroxidase, aprotinin, mushroom tyrosinase, erythropoietin, somatotropin, growth hormone, growth hormone releasing factor, galanin, urokinase, Factor IX, tissue plasminogen activator, superoxide dismutase, catalase, peroxidase, ferritin, interferon, Factor VIII and active fragments thereof.
5. The process as claimed in claim 1, wherein the amphiphile is phospholipid.
6. The process as claimed in claim 5, wherein the phospholipid has a phosphatidyl choline head group.
7. The process as claimed in claim 6, wherein the phospholipid is selected from the group consisting of phosphatidyl choline, lyso-phosphatidyl choline, sphingomyelin, hexadecyl phosphocholine and amphiphile polymers containing phosphoryl choline.
8. The process as claimed in claim 1, wherein the hydrophobic solvent is selected from the group consisting of long chain fatty acids, medium chain alcohols, branched long chain alcohols, monoglycerides, diglycerides and medium chain triglycerides.
9. The process as claimed in claim 1, wherein the amphiphile comprises phosphatidyl choline and the hydrophobic solvent is a triglyceride or wherein the amphiphile comprises lyso-phosphatidyl choline and the hydrophobic solvent is oleic acid.
10. The process as claimed in claim 1, wherein the hydrophilic solvent is water.
11. The process as claimed in claim 1, wherein the weight ratio of amphiphile to hydrophilic species is from 1:1 to 100:1.
12. The process as claimed in claim 1, wherein the hydrophilic solvent is removed by lyophilization.
13. An optically clear hydrophobic preparation of a hydrophilic species in a hydrophobic solvent prepared by a process as claimed in claim 1.
14. The preparation as claimed in claim 13, further comprising a small molecule selected from the group consisting of bile salts, pharmaceutical agents and vitamins in association with the hydrophilic species.
15. An essentially anhydrous optically clear hydrophobic preparation comprising a hydrophilic species, which is a macromolecule, and a vesicle-forming amphiphile in a hydrophobic solvent, wherein the hydrophilic species is surrounded by the amphiphile molecules with the hydrophilic head groups of the amphiphile molecules oriented towards the hydrophilic species, and wherein there is no chemical interaction between the amphiphile molecules and the hydrophilic species and the hydrophilic species is in a substantially or essentially anhydrous environment.
16. A two phase composition comprising, a hydrophilic phase and a hydrophobic phase, wherein the hydrophobic phase comprises a preparation as claimed in claim 15.
17. The composition as claimed in claim 16 which is an emulsion.
18. The composition as claimed in claim 16, wherein the hydrophobic phase is dispersed in a continuous hydrophilic phase.
19. The composition as claimed in claim 18, which is an emulsion.
20. The preparation as claimed in claim 15, further comprising a small molecule selected from the group consisting of bile salts, pharmaceutical agents and vitamins in association with the hydrophilic species.

\* \* \* \* \*